(12) United States Patent
Blankenship et al.

(10) Patent No.: US 6,509,292 B1
(45) Date of Patent: Jan. 21, 2003

US006509292B1

(54) PROCESS FOR SELECTIVE HYDROGENATION OF ACETYLENE IN AN ETHYLENE PURIFICATION PROCESS

(75) Inventors: Steven A. Blankenship, Radcliff, KY (US); Richard W. Voight, Houston, TX (US); Jennifer A. Perkins, Louisville, KY (US); James E. Fried, Jr., Buckner, KY (US)

(73) Assignee: Sud-Chemie Inc., Louisville, KY (US)

( * ) Notice: Subject to any disclaimer, the term of this patent is extended or adjusted under 35 U.S.C. 154(b) by 0 days.

(21) Appl. No.: 09/822,561

(22) Filed: Mar. 30, 2001

(51) Int. Cl.⁷ .............................. B01J 23/52; B01J 23/44
(52) U.S. Cl. .................. 502/330; 502/300; 502/325; 502/326; 502/328; 502/329; 502/332; 502/333; 502/339
(58) Field of Search ................. 502/300, 325, 502/326, 328, 329, 330, 332, 333, 339

(56) References Cited

U.S. PATENT DOCUMENTS

| | | |
|---|---|---|
| 3,156,735 A | 11/1964 | Armstrong |
| 3,442,973 A | 5/1969 | Sinfelt et al. |
| 3,974,102 A | 8/1976 | Kaiser |
| 4,126,645 A | 11/1978 | Collins |
| 4,136,062 A | 1/1979 | Boudart et al. |
| 4,329,530 A | 5/1982 | Irvine et al. |
| 4,347,392 A | 8/1982 | Cosyns et al. |
| 4,367,353 A | 1/1983 | Inglis |
| 4,404,124 A | 9/1983 | Johnson et al. |
| 4,409,410 A | 10/1983 | Cosyns et al. |
| 4,484,015 A | 11/1984 | Johnson et al. |
| 4,490,481 A | 12/1984 | Boitiaux et al. |
| 4,533,779 A | 8/1985 | Boitiaux et al. |
| 4,571,442 A | 2/1986 | Cosyns et al. |
| 5,414,170 A | 5/1995 | McCue et al. |
| 5,488,024 A | 1/1996 | Cheung et al. |
| 5,489,565 A | 2/1996 | Cheung et al. |
| 5,648,576 A | 7/1997 | Nguyen Than et al. |
| 5,889,138 A | 3/1999 | Summers |
| 5,925,799 A | 7/1999 | Stanley et al. |

FOREIGN PATENT DOCUMENTS

| | | |
|---|---|---|
| EP | 0965383 A1 | 12/1999 |
| FR | 1177764 | 4/1959 |
| FR | 2603578 | 3/1988 |
| GB | 2199588 A | 7/1988 |
| WO | WO 97/44130 | 11/1997 |

*Primary Examiner*—Elizabeth D. Wood
(74) *Attorney, Agent, or Firm*—Scott R. Cox

(57) ABSTRACT

A process for selective hydrogenation of acetylene during ethylene purification without in-situ prereduction utilizing a palladium/gold impregnated catalyst wherein the ratio of the gold to the palladium is from about 6:1 to about 50:1.

14 Claims, No Drawings

PROCESS FOR SELECTIVE HYDROGENATION OF ACETYLENE IN AN ETHYLENE PURIFICATION PROCESS

BACKGROUND OF INVENTION

1. Field of Invention

This invention relates to a process for selective hydrogenation of acetylene in an olefinic feed stream, particularly for ethylene purification. This invention also relates to a catalyst, its process of preparation and its use for the selective hydrogenation of acetylene, particularly for ethylene purification.

2. Prior Art

The manufacture of unsaturated hydrocarbons usually involves cracking various types of hydrocarbons and often produces a crude product containing hydrocarbon impurities that are more unsaturated than the desired product. These unsaturated hydrocarbon impurities are often very difficult to separate by fractionation from the desired product. A common example of this problem occurs with ethylene purification, in which acetylene is a common impurity. It is often difficult, industrially, to remove such undesirable, highly unsaturated hydrocarbons by hydrogenation without significant hydrogenation of the desired hydrocarbons. One example of this process is described in UK Pat. No. 916,056.

Two general types of gas phase selective hydrogenation processes for removing undesired, unsaturated hydrocarbons have come into use. One, known as "front-end" hydrogenation, involves passing the crude gas from the initial cracking step, after removal of steam and condensible organic material, over a hydrogenation catalyst. Despite the large hydrogen content of such gas, which is very greatly in excess of the quantity of acetylenes that are present and which quantity should be sufficient to hydrogenate a substantial part of those acetylenes, substantially complete hydrogenation of acetylene with sufficient selectivity to produce olefins of polymerization quality is often a problem. The high concentration of hydrogen present in the front-end systems requires a very selective catalyst that does not substantially hydrogenate the ethylene. Overhydrogenation can lead to a thermal excursion in reactors, known as "run-away". Under "run-away" conditions, high temperatures are experienced, severe loss of ethylene occurs and catalyst damage takes place. In addition, furnace upsets in the front-end reactor system can result in swings of CO concentration from moderate levels to very low levels. Existing front-end catalysts cannot tolerate these swings in CO concentration very well and often are prone to "run-away". In the front-end reactor system, the catalyst is also exposed to high space velocity operations 10,000–12,000 GHSV per bed. In the other type of gas phase selective hydrogenation, known as "tail-end" hydrogenation, the crude gas is fractionated and the resulting concentrated product streams are individually reacted with hydrogen in a slight excess over the quantity required for hydrogenation of the highly unsaturated acetylenes which are present. However, in tail-end use there is a greater tendency for deactivation of the catalyst, and consequently, periodic regeneration of the catalyst is necessary. Tail-end reactor systems operate at lower GHSV of 2500–5000 per bed. H2 addition can also be adjusted to maintain selectivity. However, formation of polymers is a major problem. Thermal excursion is not a problem.

A number of patents have discussed the selective hydrogenation of unsaturated hydrocarbons such as U.S. Pat. Nos. 4,126,645, 4,367,353, 4,329,530, 4,347,392 and 5,414,170.

The catalysts that are preferred for the selective hydrogenation reactions include palladium supported on an alumina substrate, as disclosed for example in U.S. Pat. Nos. 3,113,980, 4,126,645 and 4,329,530. Other gas phase palladium on alumina catalysts for the selective hydrogenation of acetylene compounds are disclosed, for example, in U.S. Pat. Nos. 5,925,799, 5,889,138, 5,648,576 and 4,126,645.

One of the problems with palladium on alumina catalysts is that under normal operating conditions not only is the acetylene hydrogenated, a substantial portion of the ethylene is also converted to ethane. In addition, these palladium on alumina catalysts often have relatively low stability due to the formation of large amounts of oligomers on the catalyst surface.

To overcome this problem, enhancers are added to the palladium which improve the catalyst properties. One common enhancer which is added to a palladium on alumina catalyst is silver. For example, conventional acetylene hydrogenation catalysts for ethylene purification comprising palladium and silver on a support material are disclosed in U.S. Pat. Nos. 4,404,124, 4,484,015, 5,488,024, 5,489,565 and 5,648,576. Specifically, U.S. Pat. No. 5,648,576 discloses a selective hydrogenation catalyst for acetylene compounds comprising from about 0.01 to 0.5 weight percent of palladium and, preferably, from about 0.001 to 0.02 percent by weight of silver. 80 percent or more of the silver is placed within a thin layer on the surface of the carrier body.

Catalysts comprising palladium, silver, an alkali metal fluoride and a support material, which are utilized for the hydrogenation of other feed stream impurities, such as dienes and diolefins, are disclosed, for example, in U.S. Pat. No. 5,489,565.

Catalysts comprising palladium and gold on a catalyst support which may be used for the hydrogenation of acetylenes and diolefins have also been suggested by U.S. Pat. Nos. 4,533,779 and 4,490,481. These patents disclose the use of a substantially greater amount of palladium than of gold, specifically 0.03 to about 1 percent by weight palladium and from 0.003 to 0.3 percent by weight gold. The ratio of the palladium to the gold is from 10:1 to about 2:1 as shown in Example 3 of both patents.

Other patents that disclose or suggest the use of palladium and gold on a carrier include U.S. Pat. No. 3,974,102 (isomerization of alpha-pinene) and U.S. Pat. No. 4,136,062 (oxidative dehydrogenation), FR 2,482,953 (U.S. Pat. No. 4,409,410 (selective hydrogenation of diolefins with silver and palladium)) and GB 802,100 (selective hydrogenation of acetylene with palladium and an element selected from the group consisting of copper, gold and silver, preferably silver).

A heterogeneous bimetallic palladium/gold catalyst for vinyl acetate production is disclosed in WO 97/44130. This catalyst is prepared by forming a first shell dispersion coating of colloidal palladium on a catalyst support surface and superimposing a second shell dispersion coating of colloidal gold metal on the first shell dispersion coating. An organometallic gold compound is employed to apply the gold dispersion on the catalyst support surface.

While conventional silver/palladium-based catalysts for the selective hydrogenation of acetylene have been useful, there are a number of problems that have been discovered from their use, including a relatively low tolerance to carbon monoxide concentration swings, lower selectivity than is desirable by the industry, and problems with high space velocity operation. Further, because the silver on these promoted catalysts reoxidizes quite easily during conventional preparation, transportation, installation and use, it is generally necessary to prereduce the silver-promoted catalyst in-situ before selective hydrogenation of the acetylene for the most efficient hydrogenation.

The catalysts of the invention are designed to address these problems and deficiencies in conventional ethylene purification catalysts.

Accordingly, it is an object of this invention to disclose a process for the selective hydrogenation of a $C_2$ and $C_3$ olefinic feed streams containing acetylenic impurities, particularly for ethylene purification.

It is a still further object of this invention to disclose a process for the front-end selective hydrogenation of acetylenic impurities, whereby the quantity of the desirable $C_2$ and $C_3$ olefins, particularly ethylene, is not substantially reduced.

It is a still further object of this invention to disclose process steps for the front end selective hydrogenation of a $C_2$ and $C_3$ olefinic feed stream containing acetylenic impurities, particularly for ethylene purification.

It is a still further object of the invention to disclose an improved palladium/gold catalyst for use in the selective hydrogenation of acetylenic impurities in front end ethylene purification.

It is a further object of the invention to disclose an improved palladium/gold catalyst containing precise quantities of palladium and gold at specific ratios on a catalyst support.

It is a further object of the invention to disclose a process for the production of a palladium/gold catalyst for the selective hydrogenation of acetylene, wherein the gold is prereduced in a wet prereduction process and does not require further reduction in-situ.

It is a still further object of the invention to disclose a palladium/gold selective hydrogenation catalyst for the selective hydrogenation of acetylene which exhibits enhanced selectivity, resistance to run-away, tolerance to CO concentration swings and improved performance at high gas hourly space velocity over conventional palladium and palladium/silver selective hydrogenation catalysts.

These and other objects can be obtained by the disclosed process for the preparation and use of a selective hydrogenation catalyst for use in a $C_2$ and $C_3$ olefinic feed stream containing acetylenic impurities particularly for ethylene purification, which is disclosed by the present invention.

SUMMARY OF THE INVENTION

The present invention is a process for the production and distribution of a catalyst for the selective hydrogenation of acetylenic impurities for ethylene purification comprising
  preparing a carrier material in a suitable shape;
  impregnating the carrier with a palladium-salt solution;
  calcining the palladium-impregnated carrier;
  impregnating the palladium-impregnated carrier with a gold-containing material;
  calcining the palladium/gold impregnated carrier;
  wet reducing the palladium and gold materials to their respective metallic states, wherein the quantity of the reduced palladium comprises from about 0.001 to about 0.028 weight percent, the amount of the gold comprises from about 0.18 to about 1.0 percent gold weight percent and the ratio of the gold to the palladium in the catalyst is in the range of about 6:1 to 50:1, and without further reduction in-situ, distributing the catalyst.

The present invention further comprises a palladium/gold loaded catalyst for front-end ethylene purification prepared by the process described above.

The invention further comprises a process for the selective hydrogenation of acetylenic impurities for ethylene purification comprising passing an ethylene feed stream, which contains acetylenic impurities, over the catalyst described above without further prereduction of the catalyst in-situ.

DETAILED DESCRIPTION

The invention is a catalyst for the selective hydrogenation of acetylene for ethylene purification. The invention further comprises a process of hydrogenation of the acetylene for ethylene purification using the catalyst of the invention. The invention further comprises a process for the production of the catalyst that is useful for the selective hydrogenation of acetylene for ethylene purification.

The catalyst of the invention is designed primarily for the selective hydrogenation of acetylene in admixture with ethylene. This type of feed stream normally includes substantial quantities of hydrogen, methane, ethane, ethylene, small quantities of carbon monoxide and carbon dioxide, as well as various impurities, such as acetylene. The goal of the selective hydrogenation is to reduce substantially the amount of the acetylene present in the feed stream without substantially reducing the amount of ethylene that is present. If substantial hydrogenation of the ethylene occurs, thermal run-away can also occur.

The catalyst of the invention exhibits improved selectivity, resistance to run-away, tolerance to CO concentration swings and improved performances at higher gas hourly space velocities (GHSV). These improvements are obtainable even if the catalyst is not prereduced in-situ by the passage of hydrogen over the catalysts. In-situ prereduction is critical to enhanced performance of conventional silver/palladium hydrogenation catalysts. However, such in-situ prereduction is not possible with certain feed streams.

The catalyst that is useful for this selective hydrogenation process is comprised of a catalyst carrier onto which palladium and gold are impregnated. The catalyst carrier may be any relatively low surface area catalyst carrier (less than 100 $m^2/g$), such as alumina, zinc oxide, nickel spinel, titania, magnesium oxide and cerium oxide. In a preferred embodiment, the catalyst carrier is an alpha alumina. The surface area of the catalyst carrier is preferably from about 1 to about 100 $m^2/g$ and more preferably from about 1 to about 75 $m^2/g$. Its pore volume is preferably in the range of about 0.2 to about 0.7 cc/g. The catalyst carrier particles can be formed in any suitable size, preferably from about 2 to about 6 millimeters in diameter. The carrier materials can also be formed in any suitable shape, such as spherical, cylindrical, trilobel and the like. In a preferred embodiment the catalyst carrier is formed in a spherical shape.

The palladium can be introduced into the catalyst carrier by any conventional procedure. The presently preferred technique involves impregnating the catalyst carrier with a palladium metal source, such as metallic palladium or an aqueous solution of a palladium salt, such as palladium chloride or palladium nitrate, preferably palladium chloride. The extent of penetration of the palladium can be controlled by adjustment of the pH of the solution. In a preferred embodiment, the depth of penetration of the palladium is controlled such that approximately 90 percent of the palladium is contained within 250 microns of the surface of the catalyst carrier. Any suitable method can be used to determine palladium penetration, such as is disclosed in U.S. Pat. Nos. 4,484,015 and 4,404,124. After palladium impregnation, the impregnated catalyst composition is calcined at a temperature from about 400 to about 600 degrees C. for about one hour.

Once the palladium-impregnated catalyst composition has been calcined, that composition is further impregnated with a gold metal source, such as metallic gold or a gold salt solution, preferably gold chloride. The palladium/gold impregnated catalyst material is then calcined at a temperature from about 400 to about 600 degrees C. for about one hour.

In an alternative embodiment the gold and palladium salts can be co-impregnated and calcined.

The metals contained in the gold/palladium catalyst precursor are then reduced, preferably by wet reducing, using a suitable wet reducing medium such as sodium formate, formic acid, hydrazine, alkali metal borohydrides, formaldehyde, ascorbic acid, dextrose and other conventional wet reducing agents.

Once the catalyst material has been reduced, it is washed with deionized water to remove chlorides to a level of less than about 100 ppm. The reduced catalyst composition is then dried at about 100 to 200 degrees C.

The amount of gold present on the catalyst after drying is from about 0.18 to about 1.0 percent, preferably 0.21 to 0.5 weight percent based on the total weight of the catalyst. The amount of the palladium present after drying is from about 0.001 to about 0.028 weight percent, preferably 0.01 to about 0.02 weight percent, based on the total weight of the catalyst. The ratio of the gold to palladium on a by-weight basis is from about 6:1 to about 50:1, preferably 12:1 to about 30:1, most preferably from about 12:1 to about 20:1.

Following the final drying step, the palladium/gold containing catalyst is ready for use in a front-end ethylene hydrogenation reactor without in-situ reduction.

In use, the catalyst is placed in a reactor. By use of the catalyst of the invention, it is not necessary to prereduce the palladium/gold catalyst in-situ before hydrogenation of the acetylene. Such in-situ prereduction is preferred for conventional silver/palladium hydrogenation catalysts. Selective hydrogenation of acetylene occurs when a gas stream containing primarily hydrogen, ethylene, methane, acetylene and minor amounts of carbon monoxide is passed over the catalyst of the invention. The inlet temperature of the feed stream is raised to a level sufficient to hydrogenate the acetylene. Generally, this temperature range is about 35 degrees C. to about 100 degrees C. Any suitable reaction pressure can be used. Generally, the total pressure is in the range of about 100 to 1000 psig with the gas hourly space velocity (GHSV) in the range of about 1000 to about 14000 liters per liter of catalysts per hour. Existing palladium/silver catalysts do not perform consistently over this range of space velocities in front-end reactor systems.

By the process of this invention, enhanced reduction of acetylene to less than 1 ppm is possible with enhanced selectivity.

Regeneration of the catalyst may be accomplished by heating the catalyst in air at a temperature, preferably not in excess of 500 degrees C., to burn off any organic material, polymers or char.

EXAMPLES

Example 1

The catalyst of this example was prepared by dipping 100 grams of a commercially available, low surface area alumina sphere with a BET surface area of 6 $m^2/g$ in a $PdCl_2$ solution to yield a palladium loading of 0.015 weight percent with palladium depth of penetration that was controlled to wherein at least about 90 percent of the palladium was within 250 microns of the surface of the spheres. After palladium impregnation, the intermediate catalyst was calcined at 454 degrees C. for 3 hours. The palladium-containing intermediate was then impregnated with $AuCl_3$ until the weight ratio between the gold and the palladium on a weight basis was 18:1. The gold loading was 0.27 weight percent. The catalyst containing the palladium and gold added materials was calcined a second time at about 454 degrees C. for 3 hours. The catalyst was then wet reduced in a 5 percent aqueous sodium formate solution heated to a temperature of 170 degrees F. for one hour. The catalyst was then washed free of chlorides (less than 100 ppm) with distilled water at 160 degrees F. The catalyst was then dried at 250 degrees F. for 18 hours.

Comparative Example 1

A commercially available, palladium/alumina catalyst manufactured by Sud-Chemie Inc. under the product name G-83A was obtained. Analysis showed that the catalyst comprised a palladium on alumina catalyst containing 0.018 weight percent palladium. The carrier was comprised of 99 weight percent alumina. The catalyst had a BET surface area of 3.7 $m^2/g$.

Comparative Example 2

A commercially available catalyst manufactured by Süd-Chemie Inc. under the product name of G-83C was obtained. Analysis showed that the catalyst comprised a palladium/silver on alumina catalyst containing 0.018 weight percent of palladium and 0.07 weight percent of silver on 99 weight percent alumina. The catalyst had a BET surface area of about 4.3 $m^2/g$.

Invention Example 2

The catalyst from Comparative Example 1 was impregnated with a solution of $AuCl_3$ to obtain a gold/palladium weight ratio of 18:1. The palladium was present at 0.018 weight percent and the gold was present at 0.32 weight percent. After impregnation the palladium/gold containing catalyst was calcined for 3 hours at 454 degrees C. The catalyst was then reduced in an aqueous solution containing 5 percent sodium formate at 170 degrees F. for 1 hour. The catalyst was then washed free of chlorides (less than 100 ppm) with dionized water at 160 degrees F. The reduced catalyst was then dried at 250 degrees F. for 18 hours.

Invention Example 3

A catalyst was prepared by dipping 100 grams of a ZnO catalyst supplied by Süd-Chemie Inc. as G-72D in a $PdCl_2$ solution to obtain a loading of 0.015 weight percent palladium. The depth of penetration of the palladium, wherein 90 percent of the palladium was present, was within 250 microns of the surface. After palladium impregnation the intermediate catalyst was calcined at 454 degrees C. for 3 hours. The palladium-containing intermediate was then impregnated with an $AuCl_3$ solution to obtain a gold/palladium weight ratio of 18:1. The amount of the gold present on the catalyst was 0.27 weight percent. The palladium/gold containing catalyst was calcined at 454 degrees C. for 3 hours. The catalyst was then reduced using a 5 percent sodium formate solution in water for one hour at 170 degrees F. The catalyst was then washed with dionized water at 160 degrees F. to remove any excess chlorides (less than 100 ppm). The reduced catalyst composition was dried at 250 degrees F. for 18 hours.

Comparative Example 3

The catalyst of Comparative Example 2 was reduced with a five percent aqueous sodium formate solution at 160 degrees F. for one hour followed by washing of the catalyst at 160 degrees F. with dionized water. The reduced catalyst was then dried for 18 hours at 250 degrees F.

TABLES

Table 1, which follows, provides a comparison of the performance of Comparative Examples 1 through 3 and Inventive Examples 1 through 3. The Examples were compared by passing a conventional ethylene feed stream over the catalyst. The catalysts were evaluated in a bench scale laboratory, one-half inch i.d. reactor tube, which simulated a front-end feed stock reactor. Catalyst activity and selectivity were evaluated. The inlet temperature, when less than 25 ppm acetylene leakage at the outlet of the reactor was observed, is considered a measurement of the catalyst activity (T1). As the temperature is increased, $C_2H_2$ is removed and some hydrogenation of $C_2H_4$ occurs resulting in a loss of selectivity. If the hydrogenation of $C_2H_4$ is significant, thermal excursion occurs (run-away). Run-away is defined as a greater than 4 percent $H_2$ loss in the system (T2). "Selectivity" is defined as T2 minus T1. A large delta T indicates a more selective catalyst. Selectivity can also be measured by the following calculations: (inlet $C_2H_2$–outlet $C_2H_2$) minus ($C_2H_6$ outlet minus $C_2H_6$ inlet)/($C_2H_2$ inlet minus $C_2H_2$ outlet) times 100. Higher numbers indicate a more selective catalyst.

Data obtained at a moderate GHSV (7000) in Table 1 illustrated enhanced selectivity for the catalyst of the invention without in-situ hydrogen prereduction. Comparative Examples 1 and 2 are a silver-promoted catalyst and a non-promoted commercially available catalyst without pre-reduction respectively. Comparative Example 3 demonstrates that wet reduction of a commercially available silver-promoted catalyst does not produce a catalyst with the same performance on the catalyst of the invention.

TABLE I

Table I-7000 GHSV activity/selectivity test

| Run | Catalyst | $T_1$ (° F.) | $T_2$ (° F.) | $T_2 - T_1$ | Selectivity at $T_1$ |
|---|---|---|---|---|---|
| Comparative Example 1 | G83A Pd/$Al_2O_3$ | 140 | 150 | 10 | +3% |
| Comparative Example 2 | G83C Pd/Ag/$Al_2O_3$ | 115 | 125 | 10 | −125% |
| Example 1 | Pd/Au/$Al_2O_3$ Wet reduced with Sodium Formate | 135 | 162 | 27 | +50% |
| Example 2 | Pd/Au/$Al_2O_3$ Wet reduced with Sodium Formate | 123 | 144 | 21 | +46.5% |
| Example 3 | Pd/Au/$Al_2O_3$ Wet reduced with Sodium Formate | 123 | 156 | 33 | +52.2% |
| Comparative Example 3 | G83C Pd/$Al_2O_3$ Wet reduced with Sodium Formate | 130 | 151 | 21 | −31.8% |

The data obtained from this analysis clearly shows the higher selectivity of the inventive examples over that of the comparative examples. Not only is there a greater T2–T1, but there are also higher selectivity values.

CO swings in concentration can lead to thermal excursions in front-end reactors with existing commercial catalysts. To predict the performance of the above-described catalysts under this condition, a test was developed to mimic CO concentration swings which often occur in ethylene plants. Each catalyst was tested under 7000 GHSV conditions. The feed consisted of 0.25 $C_2H_2$, 20% $H_2$, 250–300 ppm CO, 45% $C_2H_4$ and 34% $CH_4$. The temperature was increased until reactor exit $C_2H_2$ levels reached approximately 80 ppm. The CO level was then reduced by a mass flow controller to 61 ppm. Test results are summarized in Table II.

TABLE II

Table II-CO Swing from 250 ppm to about 61 ppm

| Run | Catalyst | CO swing | $H_2$ Consumption |
|---|---|---|---|
| Comparative Example 1 | G83A Pd/$Al_2O_3$ | 250 ppm to 61 ppm | 18.1%* |
| Comparative Example 2 | G83A Pd/Ag/$Al_2O_3$ | 250 ppm to 60 ppm | 19.1%* |
| Example 1 | Pd/Au/$Al_2O_3$ Wet reduced with Sodium Formate | 250 ppm to 60 ppm | 0.1% |

*Denotes "run-away" occurred during CO concentration swing.

The two commercially available catalysts of Comparative Examples 1 and 2 experienced thermal run away as identified by the excessive H2 consumption. The inventive Example 1 did not experience run-away conditions and thus, is more tolerant to CO reduction.

Another important feature of the invention is its ability to function under high GHSV conditions. A lab scale test was developed to predict the performance of the inventive catalysts in a commercial ethylene plant reactor that requires higher space velocities (as high as 12,000 GHSV). Table III summarizes these test results. Note that the invention (Example 1) had a reduced loss of selectivity and stable operations over the data of the comparative examples. (Comparative Examples 1 and 2). The palladium/silver catalyst of Comparative Example 2 would not run under these conditions.

TABLE III

Table III-12,000 GHSV activity/selectivity test

| Run | Catalyst | $T_1$ (° F.) | $T_2$ (° F.) | $T_2 - T_1$ | Selectivity at $T_1$ |
|---|---|---|---|---|---|
| Comparative Example 1 | G83A Pd/$Al_2O_3$ | 143 | 148 | 5 | −123.3% |
| Comparative Example 2 | G83C Pd/Ag/$Al_2O_3$ | N/A | 124 | N/A | N/A |
| Example 1 | Pd/Au/$Al_2O_3$ Wet reduced with Sodium Formate | 161 | 184 | 23 | −20.3% |

The principles, preferred embodiments, and modes of operation of the present invention have been described in the foregoing specification. The invention which is intended to be protected herein, however, is not to be construed or limited to the particular terms of disclosure, as these are to be regarded as being illustrative, rather than restrictive. Variations and changes may be made by those skilled in the art without departing from the spirit of the invention.

What is claimed is:

1. A catalyst for the selective front-end hydrogenation of acetylene comprising an inorganic support material, a palladium metal source, and a gold metal source, wherein the palladium metal source comprises from about 0.001 to about 0.028 weight percent, the gold metal source comprises from about 0.18 to about 1.0 weight percent, and wherein the ratio of the gold metal source to the palladium metal source is about 6:1 to about 50:1, wherein the weight percentages are based on the total weight of the catalyst.

2. The catalyst of claim 1 wherein at least about 90 percent of the palladium metal source is concentrated within about 250 microns of the surface of the catalyst.

3. The catalyst of claim 1 wherein the catalyst support is selected from the group consisting of alpha alumina, zinc oxide, nickel spinel and low surface area catalyst support materials with a surface area less than about 100 m²/g.

4. The catalyst of claim 1 formed in the shape of a sphere, trilobe, monolith, pellet or tablet.

5. The catalyst of claim 1 wherein the support material has a BET surface area in the range of about 1 to about 100 m²/g.

6. The catalyst of claim 1 wherein the support material has a pore volume in the range of about 0.2 to about 0.7 cc/g.

7. The catalyst of claim 1 wherein the concentration of the palladium on the catalyst is from about 0.01 to about 0.02 weight percent based on the total weight of the catalyst.

8. The catalyst of claim 1 wherein the gold metal source comprises from about 0.21 to about 0.5 weight percent based on the total weight of the catalyst.

9. The process of claim 1 wherein the ratio of the gold metal source to the palladium metal source is from about 12.1 to about 30:1.

10. The catalyst of claim 1 wherein the palladium metal source comprises from about 0.01 to about 0.02 weight percent, the gold metal source comprises from about 0.21 to about 0.5 weight percent and the ratio of the gold metal source to the palladium metal source is from about 12:1 to about 30:1 wherein the weight percentages are based on the total weight of the catalyst.

11. A process for the manufacture of a catalyst for the selective hydrogenation of acetylene without in-situ prereduction of the catalyst comprising preparing a catalyst support with a surface area less than about 100 m²/g, impregnating the catalyst support with a palladium metal source, wherein the palladium metal source is selected from the group consisting of palladium salt and metallic palladium, calcining the palladium impregnated catalyst support, impregnating the palladium impregnated catalyst support with a gold metal source, wherein the gold metal source is selected from the group consisting of a gold salt and metallic gold, calcining the palladium/gold impregnated catalyst, reducing the palladium/gold impregnated catalyst with a reducing material, and washing and drying the catalyst material, wherein the catalyst material comprises from about 0.001 to about 0.028 weight percent palladium metal source and from about 0.18 to about 1.0 weight percent of a gold metal source and wherein the ratio of the gold metal source to the palladium metal source, calculated as elemental materials, is from about 6:1 to about 50:1 based on the weight of the metallic sources, and wherein the weight percentages are based on the total weight of the catalyst.

12. The process of claim 11 wherein the depth of penetration of the palladium metal source into the catalyst support is wherein about 90 percent of the palladium is present within about 250 microns of the surface of the catalyst material.

13. The process of claim 11 wherein the catalyst is reduced using a liquid reducing medium selected from the group consisting of sodium formate, formic acid and hydrazene.

14. The process of claim 11 wherein the catalyst material comprises from about 0.01 to about 0.02 weight percent palladium metal source, from about 0.21 to about 0.5 weight percent of a gold metal source and wherein the ratio of the gold metal source to the palladium metal source is from about 12:1 to about 30:1, wherein the weight percentages are based on the total weight of the catalyst.

* * * * *